US009259556B2

(12) United States Patent
Kocaturk

(10) Patent No.: US 9,259,556 B2
(45) Date of Patent: Feb. 16, 2016

(54) MRI GUIDEWIRE

(71) Applicant: The United States of America, as represented by the Secretary, Department of Health, Washington, DC (US)

(72) Inventor: Ozgur Kocaturk, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 252 days.

(21) Appl. No.: 13/907,743

(22) Filed: May 31, 2013

(65) Prior Publication Data

US 2013/0267831 A1 Oct. 10, 2013

Related U.S. Application Data

(62) Division of application No. 12/810,481, filed as application No. PCT/US2008/088655 on Dec. 31, 2008, now Pat. No. 8,478,381.

(60) Provisional application No. 61/006,265, filed on Jan. 3, 2008.

(51) Int. Cl.
A61B 5/055 (2006.01)
A61M 25/09 (2006.01)
(Continued)

(52) U.S. Cl.
CPC .............. *A61M 25/09* (2013.01); *A61B 5/055* (2013.01); *G01R 33/287* (2013.01); *A61M 2205/3515* (2013.01); *G01R 33/34084* (2013.01)

(58) Field of Classification Search
CPC .......... A61B 5/055; A61M 2205/3515; A61M 25/09; G01R 33/34084; G01R 33/287
See application file for complete search history.

(56) References Cited

U.S. PATENT DOCUMENTS 5,792,055 A 8/1998 McKinnon
6,549,800 B1 4/2003 Atalar et al.
(Continued)

FOREIGN PATENT DOCUMENTS

WO WO 01/56469 A 8/2001
WO WO 01/73461 A 10/2001

OTHER PUBLICATIONS

Leung et al., "Intravascular MR Tracking Catheter: Preliminary Experimental Evaluation," *American Journal of Roentgeneology*, vol. 164, Jan. 1995, pp. 1265-1270.

(Continued)

*Primary Examiner* — Baisakhi Roy
(74) *Attorney, Agent, or Firm* — Klarquist Sparkman, LLP

(57) ABSTRACT

A guidewire (100) for use with interventional magnetic resonance imaging has a guidewire body (102) having a distal end and a proximal end and reserving a space therein, a dipole antenna (108) disposed in the space reserved within the guidewire body, the dipole antenna being adapted to be electrically connected to a signal processing system through a first signal channel (110) through the proximal end of the guidewire body, and a loop antenna (112) disposed in the space reserved within the guidewire body toward the distal end of the guidewire body, the loop antenna (112) being adapted to be electrically connected to the signal processing system through a second signal channel (114) through the proximal end of the guidewire body. The dipole antenna and the loop antenna are each constructed to receive magnetic resonance imaging signals independently of each other and to transmit received signals through the first and second signal channels, respectively, to be received by the signal processing system. An interventional magnetic resonance imaging system includes an active guidewire.

13 Claims, 10 Drawing Sheets

(51) Int. Cl.
*G01R 33/28* (2006.01)
*G01R 33/34* (2006.01)

(56) References Cited

U.S. PATENT DOCUMENTS

| | | | |
|---|---|---|---|
| 6,628,980 | B2 | 9/2003 | Atalar et al. |
| 7,725,161 | B2 | 5/2010 | Karmarkar et al. |
| RE42,856 | E * | 10/2011 | Karmarkar et al. ............ 600/423 |
| 8,099,151 | B2 | 1/2012 | Halperin et al. |
| 2002/0045816 | A1 | 4/2002 | Atalar et al. |
| 2003/0028094 | A1* | 2/2003 | Kumar et al. ................. 600/410 |
| 2005/0054914 | A1 | 3/2005 | Duerk et al. |
| 2006/0106303 | A1* | 5/2006 | Karmarkar et al. ............ 600/422 |
| 2008/0039709 | A1* | 2/2008 | Karmarkar .................... 600/410 |
| 2008/0097193 | A1* | 4/2008 | Karmarkar .................... 600/423 |
| 2009/0118610 | A1* | 5/2009 | Karmarkar et al. ............ 600/420 |
| 2010/0156414 | A1 | 6/2010 | Sakellariou et al. |

OTHER PUBLICATIONS

McKinnon et al., "Towards active guidewire visualization in interventional magnetic resonance imaging," *Magma*, vol. 4, No. 1, Mar. 1996, pp. 13-18.

Omary et al., "Use of Internal Coils for Independent MRI-Guided Passive Catheter Tracking and Active Guidewire Visualization," *10th Meeting Proceedings of the International Society for Magnetic Resonance in Medicine*, May 2002, 1 page.

Qiu et al., "Development of an 0.014-IN Magnetic Resonance Imaging-Guideware," *12th Meeting Proceedings of the International Society for Magnetic Resonance in Medicine*, May 2004, p. 968.

Susil et al., "Intravascular Extended Sensitivity (IVES) MRI Antennas," *Magnetic Resonance in Medicine*, vol. 50, No. 2, Aug. 2003, pp. 383-390.

* cited by examiner

MRI GUIDEWIRE

CROSS REFERENCE TO RELATED APPLICATIONS

This is a divisional of U.S. patent application Ser. No. 12/810,481, filed Jun. 24, 2010, which claimed priority to U.S. National Stage of International Application No. PCT/US2008/088655, filed Dec. 31, 2008, which was published in English under PCT Article 21(2), which in turn claims the benefit of U.S. Provisional Application No. 61/006,265, filed Jan. 3, 2008, all of the above-referenced applications being hereby incorporated by reference herein in their entirety.

BACKGROUND

1. Field of Invention

The field of this invention relates to surgical guidewires, and more particularly to surgical guidewires for use with Interventional Magnetic Resonance Imaging.

2. Discussion of Related Art

The contents of all references, including articles, published patent applications and patents referred to anywhere in this specification are hereby incorporated by reference.

Interventional Magnetic Resonance Imaging ("iMRI") has increased in interest during the last decade due to the advent pulse sequence improvements, Magnetic Resonance ("MR") compatible instruments, the development of rapid imaging techniques and automatic instrument tracking techniques.

For MR guidance of vascular interventions to be safe, the interventionalist must be able to visualize the tip location and distal shaft of the MRI compatible guidewire relative to the vascular system and surrounding anatomy. A number of instrument visualization approaches under MRI have been developed including both passive and active techniques. Passive visualization techniques rely on the creation of susceptibility artifacts to enhance the device (e.g., catheter) appearance by using contrast agents or ferromagnetic materials. Active visualization relies on supplemental hardware embedded into a catheter body such as a Radio Frequency ("RF") antenna to receive the RF signal during MRI (Susil R C, Yeung C J, Atalar E, "Intravascular extended sensitivity (IVES) MR imaging antennas." Magnetic Resonance in Medicine, 2003; 50(2): 383-390). However, none of these techniques provides satisfactory results in terms of both instrument tip and shaft visualization at the same time. Visualization of the shaft only is not enough to advance a guidewire through tortuous vessels due to the risk of puncturing vessel walls and visualization of a single point is not sufficient for steering an active guidewire in complex vessel territory (Atalar E, Kraitchman D L, Carkhuff B, Lesho J, Ocali O, Solaiyappan M, Guttman M A, Charles H K, Jr. Catheter-tracking FOV MR Fluoroscopy. Magnetic Resonance in Medicine 1998; 40(6):865-872).

Interventional MR Imaging

Magnetic Resonance Imaging (MRI) is one of the most important clinical imaging modalities. A significant advantage of using MRI in clinical procedures is that imaging via MR is conducted only using a strong homogenous magnetic field and radio frequency energy pulses, without the use of harmful ionizing radiation such as with the use of X-ray angiography. Also, MRI utilizes Nuclear Magnetic Resonance principles with gradient coil elements to provide spatial encoding, resulting in the ability to perform 3-D human body imaging with high soft tissue contrast (Lauterbur P C. NMR Imaging in Biomedicine. Cell Biophysics 1986; 9(1-2): 211-214; Lai C M, Lauterbur P C. True Three-Dimensional Image Reconstruction by Nuclear Magnetic Resonance Zeugmatography. Physics in Medicine and Biology 1981; 26(5):851-856; Kramer D M, Schneider Js, Rudin A M, Lauterbur P C. True Three-Dimensional Nuclear Magnetic Resonance Zeugmatographic Images of a Human Brain. Neuroradiology 1981; 21(5):239-244). MRI allows one to obtain information about various physical parameters such as flow, motion, magnetic susceptibility and temperature (Axel L. Blood Flow Effects in Magnetic Resonance Imaging. Magnetic resonance Annual 1986; 237-244; Henkelman R M, Stainsz G J, Graham S J. Magnetization Transfer in MRI: A review. NMR Biomedicine 2001; 14(2):57-64; Dickenson R J, Hall A S, Hind A J, Young I R. Measurement of Changes in Tissue Temperature using MR Imaging. Journal of Computer Assisted Tomography 1986; 10(3):468-472). Because of this, MRI has a wide variety of both diagnostic and therapeutic imaging applications both in the clinical and research environment. When MRI was initially introduced in the clinical environment, it was used for only diagnostic imaging purposes with almost no consideration for use in therapeutic procedures (Webb W R, Gamsu G, Stark D D, Moon K L, Jr., Moore E H. Evaluation of Magnetic Resonance Sequences in Imaging Mediastinal Tumors. American Journal of Roentgenology 1984; 143(4):723-727; Belli P, Romani M, Magistrelli A, Masetti R, Pastore G, Costantini M. Diagnostic Imaging of Breast Implants: Role of MRI. Rays 2002; 27(4):259-277). Reasons for this can be attributed to the lack of sequences designed for interventional MRI such as sequences for real-time device tracking, sequences that provide image contrast that correlate directly to therapy performance, high-speed sequences that allow real-time imaging with sufficient contrast and resolution and the lack of dedicated and optimized hardware for interventional applications.

In recent years, efforts have been made to develop MRI as an interventional tool for image guided interventions by addressing the above mentioned challenges (Miles K. Diagnostic and Therapeutic Impact of MRI. Clinical Radiology 2002; 57(3):231-232; Jolesz F A, Blumenfeld S M. Interventional Use of Magnetic Resonance Imaging. Magnetic Resonance Quarterly 1994; 10(2):85-96; Jolesz F A. Interventional and Intraoperative MRI: A General Overview of the Field. Journal of Magnetic Resonance Imaging 1998; 8(1):3-7). Also, development of 1.5 T magnets with short bores that allow access to the groin area for catheter-based procedures, liquid crystal image displays that can be exposed to high magnetic fields, improvements in the hardware of the magnetic field gradient systems for additional gains in image acquisition speed, the development of catheter based MRI antennas for localized intravascular signal reception provide wide range of interventional MR Imaging applications.

MRI Compatible and Visible Devices for Interventional Procedures

MR guided interventions can only be performed with devices free of ferromagnetic components, otherwise as one would encounter severe magnetic forces (induced displacement force and torque) on the device by the static magnetic field of the MR scanner and they would also cause image distortion (Shunk K A, Iima J A, Heldman A W Transesophageal magnetic resonant imaging. Magn Reson. Med 1999; 41:722-726). However, MR compatible and safe devices are not enough to perform vascular interventions with MRI. The reliable visualization of these devices in relation to the surrounding tissue morphology is also required. In contrast to ultrasound, X-ray fluoroscopy, or computed tomography (CT), visualization of interventional instruments in MR has proven to be difficult. A number of approaches have been developed for depicting vascular instruments in an MR environment. They can be broadly grouped into two categories: passive and active visualization.

Passive Visualization

In passive visualization techniques, achieving adequate catheter contrast is based on enhancing the inherent signal void of an instrument as it displaces spins during insertion. Differences in magnetic susceptibility can be used to create large local losses in signal due to intra-voxel dephasing (Rubin D L, Ratner A V, Young S W. Magnetic susceptibility effects and their application in the development of new ferromagnetic catheters for magnetic resonance imaging. Invest radiol. 1990; 25:1325-1332). The tip or body of passive catheters is composed of either ferromagnetic or paramagnetic sleeves that produce susceptibility artifacts. Incorporating multiple rings of paramagnetic dysprosium oxide ($Dy_2O_3$) along the instrument tip allows the catheter to be consistently visualized independently of orientation (see FIG. 1) (Bakker C J, Hoogeveen R M, Hudak W F, van Vaals J J, Viergever M A, Mali W P. MR-guided endovascular interventions:susceptibility-based catheter and near real time imaging technique).

Susceptibility markers must have a high magnetic moment to induce an adequate artifact at a variety of scan techniques and tracking speeds. In other words, they must have sufficient contrast to noise ratio (CNR) with respect to the background in order to distinguish the device in thick slab images. The CNR can be calculated as $$CNR = -\frac{S_m}{\sigma_s} \quad (1)$$

With $S_m$ the signal loss induced by the marker, which is negative in the subtraction image, and $\sigma_s$ is the noise in the background of the subtraction image. Because an MR scanner provides a strong magnetic field with applied gradients, the passive marker material is magnetized homogenously. So, the magnetic moment (m) can be directly related to $B_0$ (Teitz J R, Miltford F J and Christy R W 1993 Foundations of Electromagnetic Theory $4^{th}$ edn (Reading, Mass.: Addison-Wesley) p 245). This relation can be written as $$m(B_0)=\Delta M(B_0)V \quad (2)$$

with $\Delta M$ the magnetization difference between the marker and tissue and V the volume of the marker. For diamagnetic and paramagnetic materials, m is proportional to $B_0$. For other types of magnetism like ferro- and ferrimagnetism, a nonlinear relation exists. For a marker of subvoxel volume, the field distortion can be approximated by a dipole field (Bos C, Viergever M A and Bakker c J G 2003 On the artifact of a subvoxel susceptibility deviation in spoiled gradient-echo imaging Magn. Reson. Med. 50 400-4)

$$\Delta B_z(x, y, z) = \frac{\mu_0 m(B_0)}{4\pi} \frac{2z^2 - y^2 - x^2}{(x^2 + y^2 + z^2)^{\frac{5}{2}}} \quad (3)$$

with $\mu_0$ the permeability in free space and x, y and z the spatial coordinates with $\Delta B_z$ and $B_0$ in the z-direction. The magnetic moment of the marker needs to be large with regard to the size of the marker and CNR of the artifacts. This excludes diamagnetic and weakly paramagnetic materials, since their magnetization is too low to create a large magnetic moment with only a small amount of material (Schenck J F 1996 the role of magnetic susceptibility in magnetic resonance imaging: MRI magnetic compatibility of the first and second kinds Med. Phys. 23 815-50). High tracking speeds can be achieved when short echo times are used, and this requires an even higher magnetic moment for heavy $T_2^*$-weighting around the marker. Then, strongly paramagnetic markers become bulky in order to realize an adequate magnetic moment. Biocompatibility and safety can be achieved by embedding into another medium, e.g. the coating of the device. Again, easily magnetizable materials are preferred, since a lower concentration of marker material is needed. The optimal applicability regarding field strength may be realized with a field-strength-independent magnetic moment of the marker. Such a nonlinear magnetic property is partly exhibited by ferro- and ferromagnetic materials. The advantage of using a passive marker is that circuit components and transmission lines are not required to visualize the catheter. This property of passive visualization techniques is really important because it also eliminates electrical safety issues. However, this technique also has several disadvantages. First of all, it provides low spatial resolution. Secondly, it slows down the speed of the procedure compared to active tracking methods. And finally, a susceptibility artifact varies based on device orientation and magnetic field strength.

Active Visualization

Active visualization relies on the incorporation of a miniature solenoid coil into the device itself (Dumoulin C L, Souza Sp, Darrow R D. Real-time position monitoring of invasive devices using magnetic resonance. Magn reson. Med. 1993; 29: 411-415; Ladd M E, Zimmerman G G, MckInnon G C, von Schulthess G K et al. Visualization of vascular guidewires using MR tracking. J Magn Reson Imaging 1998; 8:251-253; Leung D A, debatin J F, Wildermuth S, McKinnon G C et al. Intravascular MR Tracking catheter: preliminary experimental evaluation. Am J roentgenol 1995; 164:1265-1270). The coil is connected to the scanner via a thin coaxial cable passing through the catheter and provides a robust signal, identifying the instrument location with high contrast. The tip of an active catheter can be visualized with high contrast by the incorporated coil on the tip.

Loop Antenna: Solenoid Coil

A solenoid coil is basic form of loop antenna element in which the wire is coiled in a helical pattern to create a cylindrical shape as shown in FIG. 2. Solenoid micro coils can be connected to the MR systems through the use of coaxial transmission lines, which may serve both detuning and signal transduction purposes. Loop antenna signal sensitivity for small-loop receivers falls off very rapidly ($1/r^3$, where r is the radial distance from the loop) (Balanis C A. Antenna theory. New York: John Wiley & Sons; 1997. 941 p.). To improve longitudinal coverage, long-loop intravascular antennas were subsequently investigated (Atalar E, Bottomley P A, Ocali O, Correia L C, Kelemen M D, Lima J A, Zerhouni E A. High resolution intravascular MRI and MRS by using a catheter receiver coil. Magn Reson Med 1996; 36:596-605). For these long, narrow loop receivers (in which the loop length is much greater than its width), sensitivity falls off as $1/r^2$. Despite improved longitudinal coverage, these receivers produce limited SNR when conductor separation is small as can be seen in FIG. 3.

Loop Antenna: Opposed Solenoid Coil

The opposed solenoid loop antenna is based on groups of helical loops separated by a gap region, with current driven in opposite directions in the helical loops on either side of the gap, as shown in the schematic of FIG. 4. The gap provides the small area of homogenous longitudinal magnetic field that makes it a good candidate for especially using as an imaging coil within and beyond the vessel wall. However, it has a small area of homogenous longitudinal coverage compared with the dipole antenna.

Dipole Antenna

A dipole antenna for iMRI applications can be a simple coaxial transmission line with an extended inner conductor. Dipole antenna sensitivity falls off as 1/r where r is the radial distance from the antenna center (Susil R C, Yeung C J, Atalar E, "Intravascular extended sensitivity (IVES) MR imaging antennas." Magnetic Resonance in Medicine, 2003; 50(2): 383-390).

Dipole antenna sensitivity can be improved by increasing the insulation layer (insulation broadens the SNR distribution) and helical winding over the extended core inductor (winding allows for improved SNR near the tip of the antenna). A dipole antenna appearance in a water filled phantom under MR Imaging can be seen in FIG. 5.

SUMMARY

Further objects and advantages will become apparent from a consideration of the description, drawings and examples.

A guidewire for use with interventional magnetic resonance imaging according to an embodiment of the current invention has a guidewire body having a distal end and a proximal end and reserving a space therein, a dipole antenna disposed in the space reserved within the guidewire body, the dipole antenna being adapted to be electrically connected to a signal processing system through a first signal channel through the proximal end of the guidewire body, and a loop antenna disposed in the space reserved within the guidewire body toward the distal end of the guidewire body, the loop antenna being adapted to be electrically connected to the signal processing system through a second signal channel through the proximal end of the guidewire body. The dipole antenna and the loop antenna are each constructed to receive magnetic resonance imaging signals independently of each other and to transmit received signals through the first and second signal channels, respectively, to be received by the signal processing system.

An interventional magnetic resonance imaging system according to an embodiment of the current invention has a magnetic resonance imaging scanner, an active guidewire disposed proximate the magnetic resonance imaging scanner, the active guidewire having a dipole antenna and a loop antenna, and a signal processing system in communication with the active guidewire to receive a first signal from the dipole antenna through a first signal channel and to receive a second signal through a second signal channel from the loop antenna.

BRIEF DESCRIPTION OF THE DRAWINGS

The invention is described herein, by way of example only, with reference to the accompanying figures, in which like components are designated by like reference numerals, in which.

DETAILED DESCRIPTION

Figure 1:
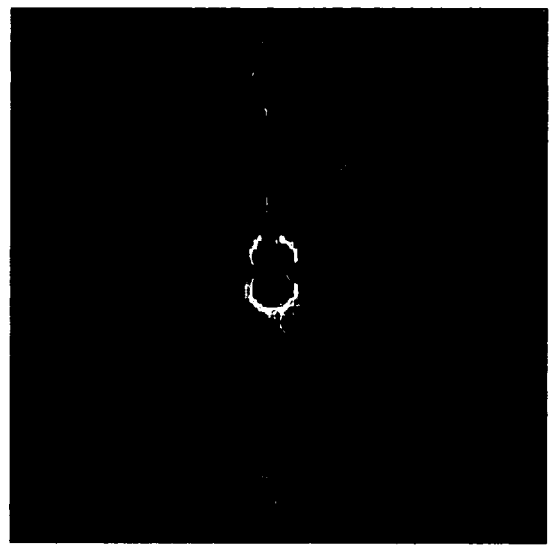
FIG. 1 shows an induced artifact at the tip of the guidewire in b-SSFP acquisition with flip angle α=5° guidewire placed in a phantom that has NaCl solution (see, Ralf Mekle, Eugen Hofmann, Klaus Scheffler, A polymer Based Mr Compatible Guidewire: A Study to explore new Prospect for Interventional Peripheral Magnetic resonance Angiography Journal of Mag. Reson. Imaging 23:145-155 (2006))
Figure 2:
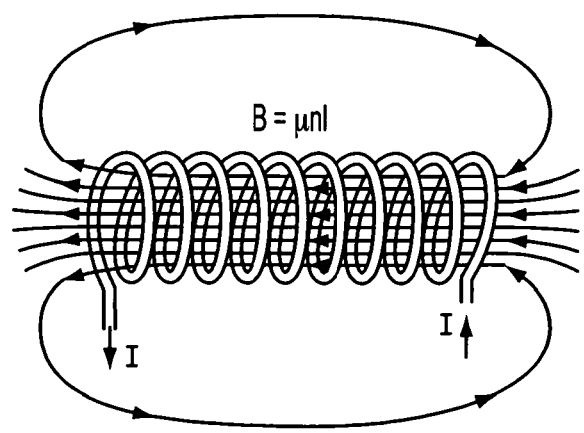
FIG. 2 is a schematic representation of a solenoid coil overlaid on a field line plot.
Figure 3:
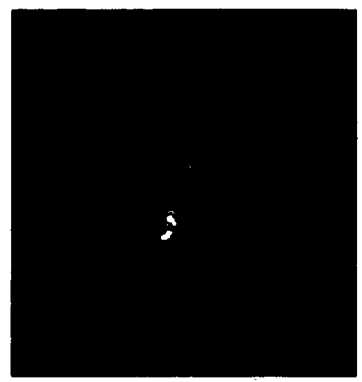
FIG. 3 shows a porcine imaging catheter tracking experiment in vivo using the loop coil (Claudia M., Hillenbrand, Daniel R. Elgort, Eddy Y. Wong et al. Active Device Tracking and High Resolution Intravascular MRI using a Novel Catheter-Based, Opposed-Solenoid Phased Array Coil. Magn Reson. Medicine 2004; 51:668-675)
Figure 4:
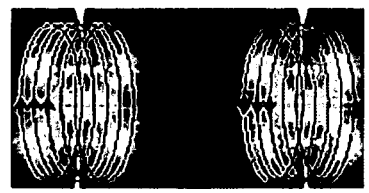
FIG. 4 shows an opposed solenoid coil configuration overlaid on a field sensitivity plot.
Figure 5:
FIG. 5 is the image of a water filled phantom acquired using both body coil and dipole antennas in which the signal received from dipole antenna is colored using special software.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

The embodiments illustrated and discussed in this specification are intended only to teach those skilled in the art the best way known to the inventors at the time of filing to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

The current invention relates to the iMRI guidewires in which antennas embedded into guidewire bodies are used for signal reception. A receiving antenna is positioned within the imaging volume that is used to detect the MR signal generated from the patient as the excited spins relax back into an equilibrium distribution. Current methods for active device tracking involve the use of single or multiple tuned Larmour frequency microcoils (loop antenna) integrated into the tip of a catheter or loop-less antenna to provide device position or position and orientation.

Embodiments of the current invention are directed to a clinical grade 0.035" multi purpose guidewire that can offer both precise tip location and distal shaft visualization. Various structures may include the following:

(1) Using separate RF signal receiving channels connected to individual RF antennas designed for tip localization and shaft visualization with
 (a) coaxially placed two separate antennas within guidewire body;
 (b) coaxially placed two antennas that share one antenna element in common.

(2) Embedding one antenna design into guidewire body to visualize wire shaft and designing a guidewire tip that causes a susceptibility artifact at very distal tip while keeping all the mechanical properties same. In previous studies, the susceptibility artifact used as a marker was at least 5-9 cm away from the distal tip (J. M. Serfaty, X. Yang, P. Aksit, H. H. Quick, M. Solaiyappan, E. Atalar, Toward MRI-guided Coronary Catheterization: Visualization of Guiding Catheters, Guidewires, and Anatomy in Real Time. Invited. Journal of Magnetic Resonance Imaging, (4):590-594, 2000). However, in the case of tip deflection of the guidewire during advancement, this kind of approach fails to indicate where the exact tip location of the guidewire is under MRI.

Figure 6:
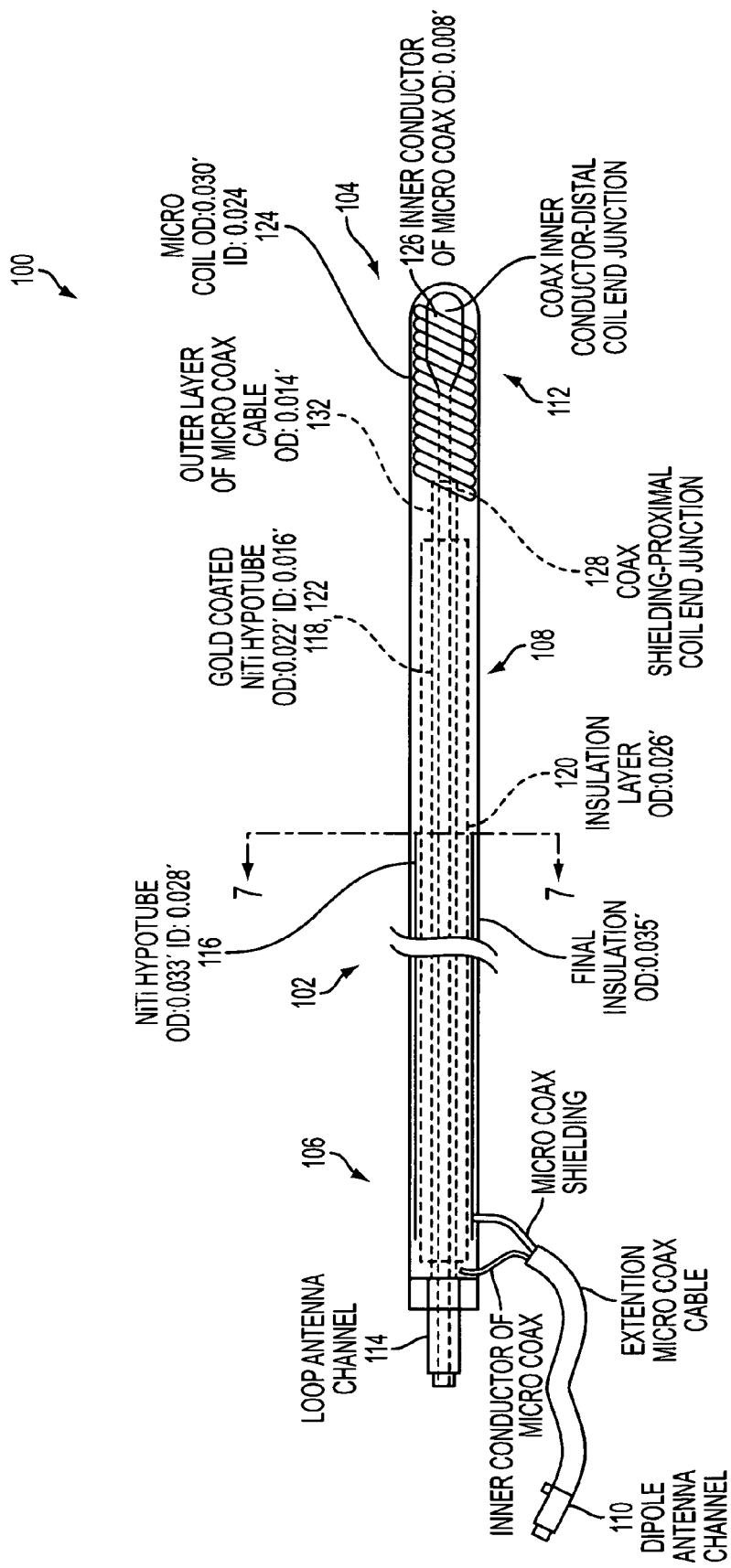
FIG. 6 is a schematic illustration of a guidewire according to an embodiment of the current invention.

A guidewire 100 for use with interventional magnetic resonance imaging according to an embodiment of this invention is illustrated schematically in FIG. 6. The guidewire 100 has a guidewire body 102 having a distal end 104 and a proximal end 106, in which the guidewire body 102 reserves a space therein. The guidewire 100 has a dipole antenna 108 disposed in the space reserve by the guidewire body 102. The dipole antenna 108 is adapted to be electrically connected to a signal processing system through a first signal channel 110 through the proximal end 106 of the guidewire body 102. A loop antenna 112 is disposed in the space reserve within the guidewire body 102 of the guidewire 100. The loop antenna 112 is adapted to be electrically connected to a signal processing system through a second signal channel 114 through the proximal end 106 of the guidewire body 102. The dipole antenna 108 and the loop antenna 112 are each constructed to receive magnetic resonance imaging signals independently of each other and to transmit the received signals through the first 110 and second 114 signal channels, respectively.

Figure 7:
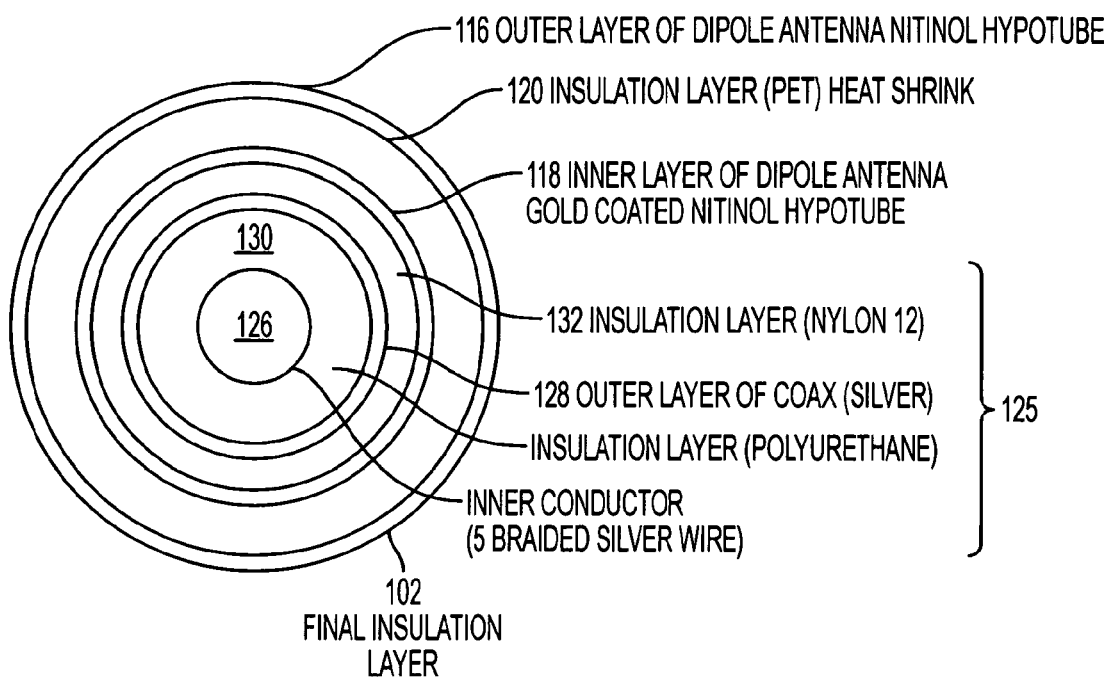
FIG. 7 is a cross sectional view of the guidewire illustrated in FIG. 6 taken along the cut line as indicated.

FIG. 7 is a cross-sectional view of a portion of the guidewire 100 taken along the cross-section indicated in FIG. 6. As one can see illustrated schematically in FIGS. 6 and 7 taken into conjunction, the guide wire 100 includes an outer hypotube 116, an inner hypotube 118 and an insulation layer 120 disposed between the inner hypotube and the outer hypotube. The inner hypotube 118 extends beyond a distal end of the outer hypotube 116 in a direction of the distal end 104 of the guidewire 100 to provide a whip portion 122 of the dipole antenna 108. The inner hypotube 118 and outer hypotube 116 may be selected from materials suitable for use with active magnetic resonance imaging. For example, Nitinol has been found to be a suitable material for the inner hypotube 118 and outer hypotube 116. Furthermore, one may coat the whip portion 122 of the dipole antenna 108 with a good electrical conductor. For example, a gold coated whip portion 122 of the inner hypotube 118 has been found to work well according to an embodiment of the current invention. The whip portion 122 of the dipole antenna 108 may be selected to have a length suitable to receive signals at a Larmour frequency during operation of the magnetic resonance imaging system.

The loop antenna 112 may include a microcoil 124 according to an embodiment of this invention. The microcoil 124 of the loop antenna 112 is electrically connected to the second signal channel 114 by a micro coaxial cable 125 that runs along a space reserved within the center of the dipole antenna 108. The micro coaxial cable 125 has an inner conductor 126 that is electrically connected to a distal end of the microcoil 124 and an outer conductive layer 128 connected to an opposing end of the microcoil 124. An insulation layer 130 separates the inner conductor 126 and the outer conductor 128 of the micro coaxial cable 125. In one example, the inner conductor 126 is five braided silver wires and the outer conductor 128 is also composed of silver. However, the invention is not limited to only these specific materials and structures. Polyurethane has been found to be one suitable material for the insulation layer 130 of the micro coaxial cable. An insulation layer 132 is disposed between the micro coaxial cable 125 and an inner surface of the dipole antenna 108. Nylon 12 was found was found to be a suitable material for the insulation layer 132.

Figure 8:
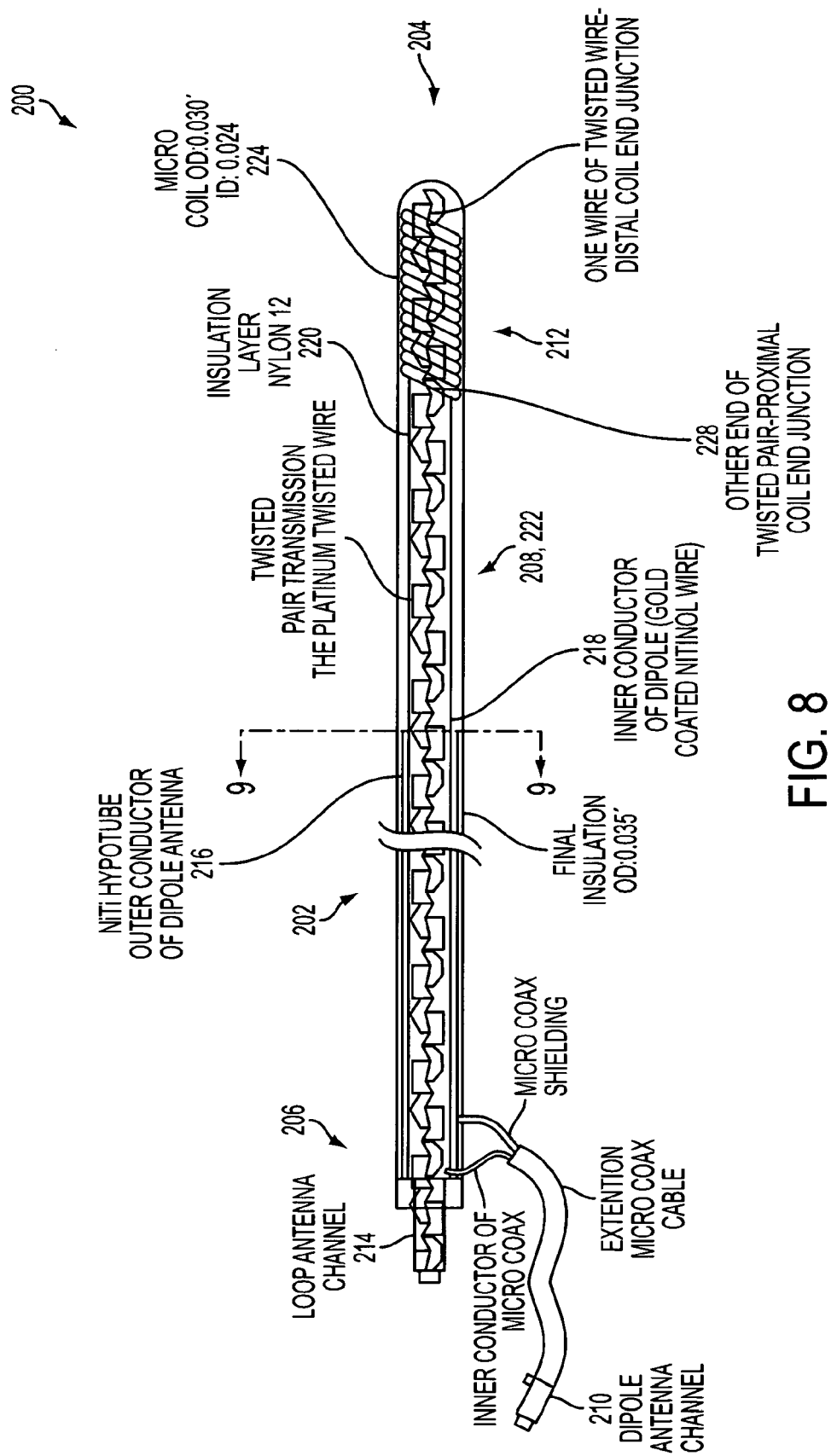
FIG. 8 is a schematic illustration of a guidewire according to an embodiment of the current invention.

FIG. 8 is a schematic illustration of a guidewire 200 according to another embodiment of the current invention. The guidewire 200 has a guidewire body 202 having a distal end 204 and a proximal end 206, in which the guidewire body 202 reserves a space therein. The guidewire 200 has a dipole antenna 208 disposed in the space reserve by the guidewire body 202. The dipole antenna 208 is adapted to be electrically connected to a signal processing system through a first signal channel 210 through the proximal end 206 of the guidewire body 202. A loop antenna 212 is disposed in the space reserve within the guidewire body 202 of the guidewire 200. The loop antenna 212 is adapted to be electrically connected to a signal processing system through a second signal channel 214 through the proximal end 206 of the guidewire body 202. The dipole antenna 208 and the loop antenna 212 are each constructed to receive magnetic resonance imaging signals independently of each other and to transmit the received signals through the first 210 and second 214 signal channels, respectively.

Figure 9:
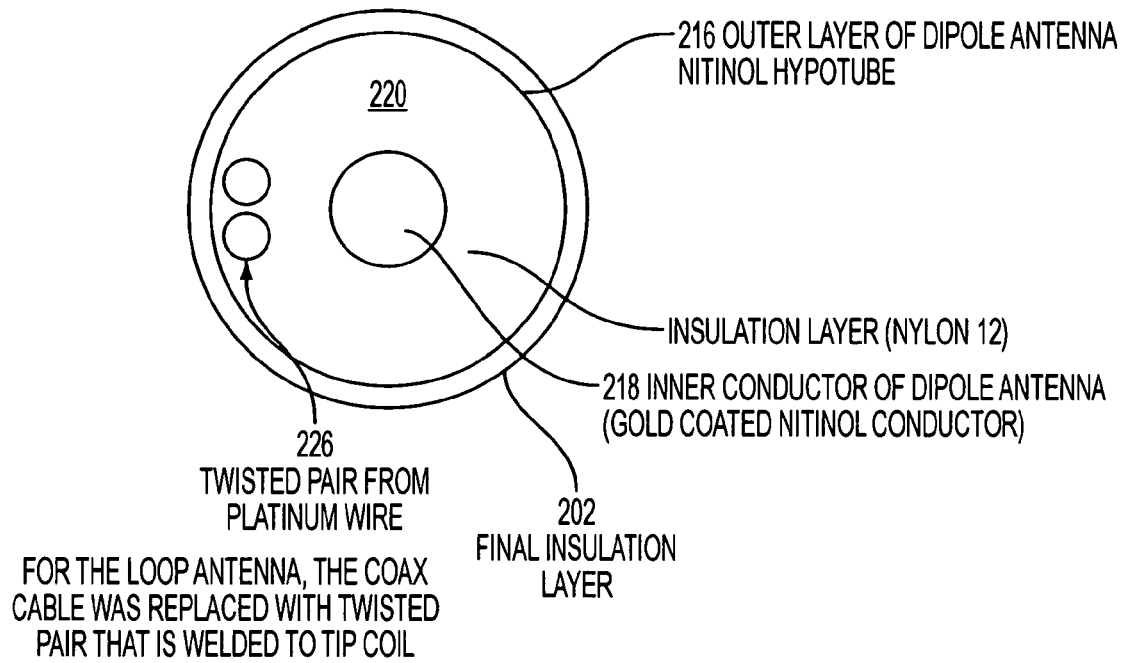
FIG. 9 is a cross sectional view of the guidewire illustrated in FIG. 8 taken along the cut line as indicated.

FIG. 9 is a cross-sectional view of a portion of the guidewire 200 taken along the cross-section indicated in FIG. 8. As one can see illustrated schematically in FIGS. 8 and 9 taken into conjunction, the guide wire 200 includes an outer hypotube 216, an inner conductor 218 and an insulation layer 220 disposed between the inner hypotube and the outer hypotube. The inner conductor 218 extends beyond a distal end of the outer hypotube 216 in a direction of the distal end 204 of the guidewire 200 to provide a whip portion 222 of the dipole antenna 208. The inner conductor 218 and outer hypotube 216 may be selected from materials suitable for use with active magnetic resonance imaging. For example, Nitinol has been found to be a suitable material for the inner conductor 218 and outer hypotube 216. Furthermore, one may coat the whip portion 222 of the dipole antenna 208 with a good electrical conductor. For example, a gold coated whip portion 222 of the inner conductor 218 has been found to work well according to an embodiment of the current invention. The whip portion 222 of the dipole antenna 208 may be selected to have a length suitable to receive signals at a Larmour frequency during operation of the magnetic resonance imaging system.

The loop antenna 212 may include a microcoil 224 that is electrically connected to the second signal output channel 214 by a twisted pair of electrical conductors 226 in this embodiment of the current invention. The twisted pair of electrical conductors 226 can extend along a central pathway or within intermediate insulation layers of the guidewire 200.

As one can see in the cross-sectional view of FIG. 9, the twisted pair of wires 226 in this example are within the insulation layer 220 disposed between the inner conductor 218 and outer hypotube 216 of the dipole antenna 208. Platinum wires were found to be suitable for the twisted pair of wires 226. The guidewire 200 according to this embodiment of the current invention can provide more mechanical flexibility than that of the embodiment of FIGS. 6 and 7.

Figure 10:
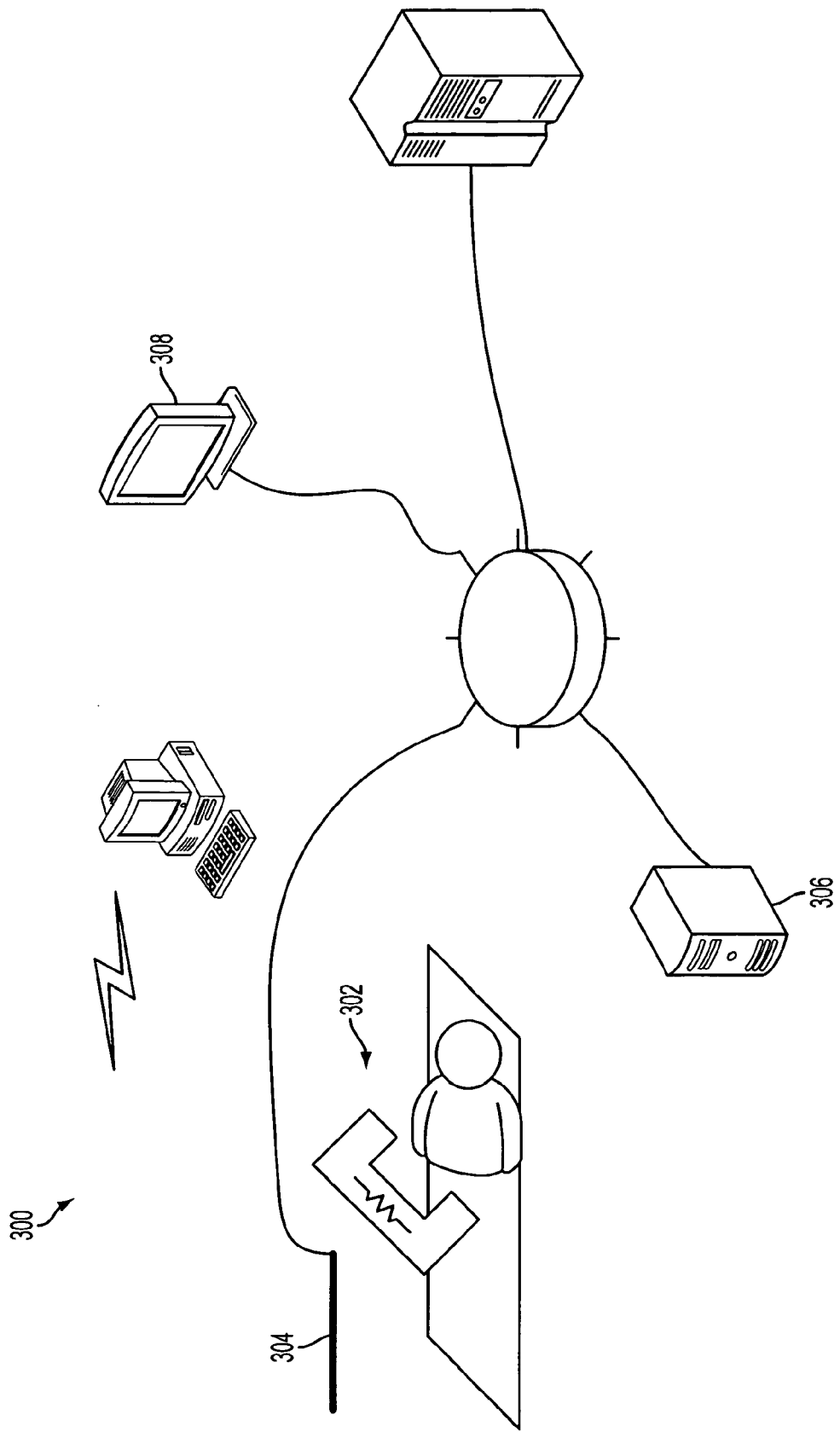
FIG. 10 is a schematic illustration of an interventional magnetic resonance imaging system according to an embodiment of the current invention.

FIG. 10 illustrates an interventional magnetic resonance imaging system 300 according to an embodiment of the current invention. The interventional magnetic resonance imaging system 300 may include a magnetic resonance imaging scanner 302, an active guidewire 304 proximate the magnetic resonance imaging scanner 302, and a signal processing system 306 electrically connected to the active guidewire 304 through first and second signal channels. First and second tuning circuits (not shown) are electrically connected to the active guidewire. The first and second tuning circuit may be incorporated as part of the signal processing unit 306, or may be electrically connected to the signal processing unit 306 and active guidewire 304. The active guidewire 304 is constructed to provide signal information indicative of an extended portion of a shaft portion of the active guidewire 304 through the first signal channel during operation of the magnetic resonance imaging scanner 302 and the active guidewire 304 is constructed to provide signal information indicative of a distal end of the active guidewire 304 through a second signal channel during operation of the magnetic resonance imaging scanner 302. In some embodiments of the current invention, the active guidewire 304 may be guidewire 100 and/or 200 as illustrated in FIGS. 6 through 9. In addition, the interventional magnetic resonance imaging system 300 may include a display system 308 that is in communication with the receiver system 306 such that the display system may display a real time image corresponding to the active guidewire 304 during a surgical procedure. Further components such as various data recording and storage units may also be included, as desired. Also, the various components of the system may be hard-wired together or may be in communication through wireless communications links.

Example

Two Channel Active 0.035" Guidewire Design

The tip and shaft visualization of the 0.035" guidewire at the same time is quite challenging due to the dimensional restrictions. A hollow shaft dipole antenna should be designed that can be tuned to the Larmour Frequency to provide antenna designs to visualize both tip and shaft during real time MR imaging. The dipole antenna will be designed to visualize the shaft of the 0.035" guidewire due to its high longitudinal sensitivity. For such a loopless antenna, all of the antenna capacitance exists between the two poles of the antenna, with the body and antenna insulation acting as the dielectric. With added insulation, the current profile on the antenna is broadened and thus charge density is decreased. This reduced charge density results in lower electric fields and less power deposition in the body, and hence a reduced contribution to noise resistance. At the same time, however, there is an increase in the amount of tissue wherein "magnetic losses" occur (i.e., the amount of tissue containing eddy currents) (B. Qiu, A. El-Sharkawy, V. Paliwal, P. Karmarkar, F. Gao, E. Atalar, X. Yang, Simultaneous RF Heating and MR Thermal Mapping Using An Intravascular MR-Imaging/RF-Heating System, iMRI 2004, Boston, Mass.), because of the broadening of the current distribution. This effect will tend to raise noise resistance, offsetting the decrease due to the distributed capacitance effect. Considering both of these effects, there is little net change in SNR with the addition of antenna insulation. It means that the dipole antenna can keep its visibility performance after the heat shrink insulation layer and hydrophilic coating is added over the guidewire shaft.

A hollow shaft dipole antenna design allows enough space to embed a loop antenna into the guidewire body to visualize the precise guidewire tip location.

The Criteria for Dipole Antenna Design in an Embodiment of the Invention

Nitinol material is the best material candidate for designing the dipole antenna among other MRI compatible materials such as platinum, titanium and cobalt-chromium due to its MRI compatible and mechanical properties. However, because nitinol is not a good conductor, there are several factors that can be considered carefully to end up with an efficient dipole antenna.

Characteristic Impedance

Figure 11:
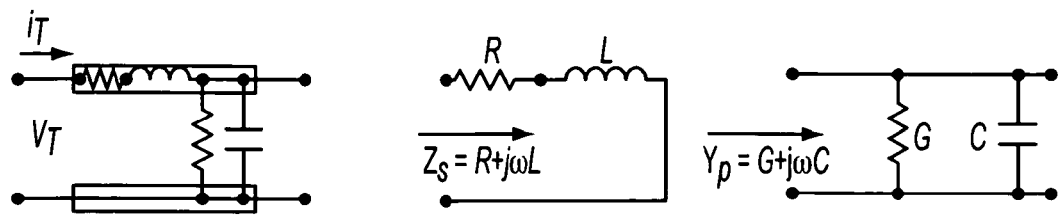
FIG. 11 helps illustrate a concept that a characteristic impedance of a transmission line can be derived from short-circuited series impedance and open-circuited shunt admittance of its incremental segment.

For all Transverse Electric and Magnetic mode transmission lines a simplified theoretical analysis may begin with the equivalent circuit in which each incrementally small length of line is modeled as a series of impedance and a shunt admittance that can be seen in FIG. 11. A wave traveling along the line has voltage, $V_T$, and current, $i_T$, related by the characteristic impedance of the line segment, $Z_{TL}$ (Sinnema, W., Electronic Transmission Technology, $2^{nd}$ ed., Englewood Cliffs, N.J., Prentice Hall, 1988).

$$Z_{TL} = \frac{v_T}{i_T} = \sqrt{\frac{Z_s}{Y_p}} = \sqrt{\frac{R + j\omega L}{G + j\omega C}} \tag{4}$$

The inductance and capacitance value of a transmission line depends on the type of material and the dimensions. And characteristic impedance of the Nitinol coaxial transmission line should be at least around 20-30Ω to make the impedance matching process feasible.

Return Loss

The reflection coefficient, Γ, is defined to show what fraction of an applied signal is reflected when a $Z_0$ source drives a load of $Z_L$. Forward and reflected traveling waves inside a transmission line can be separated and measured by using directional couplers. The reflection coefficient is a ratio of two normalized traveling voltage waves. Its magnitude squared represents the reflected power. Converted to decibels, it is called the return loss, $$RL_{dB} = 10(\log|\Gamma|^2) = 20(\log|\Gamma|) \tag{5}$$

Figure 12:
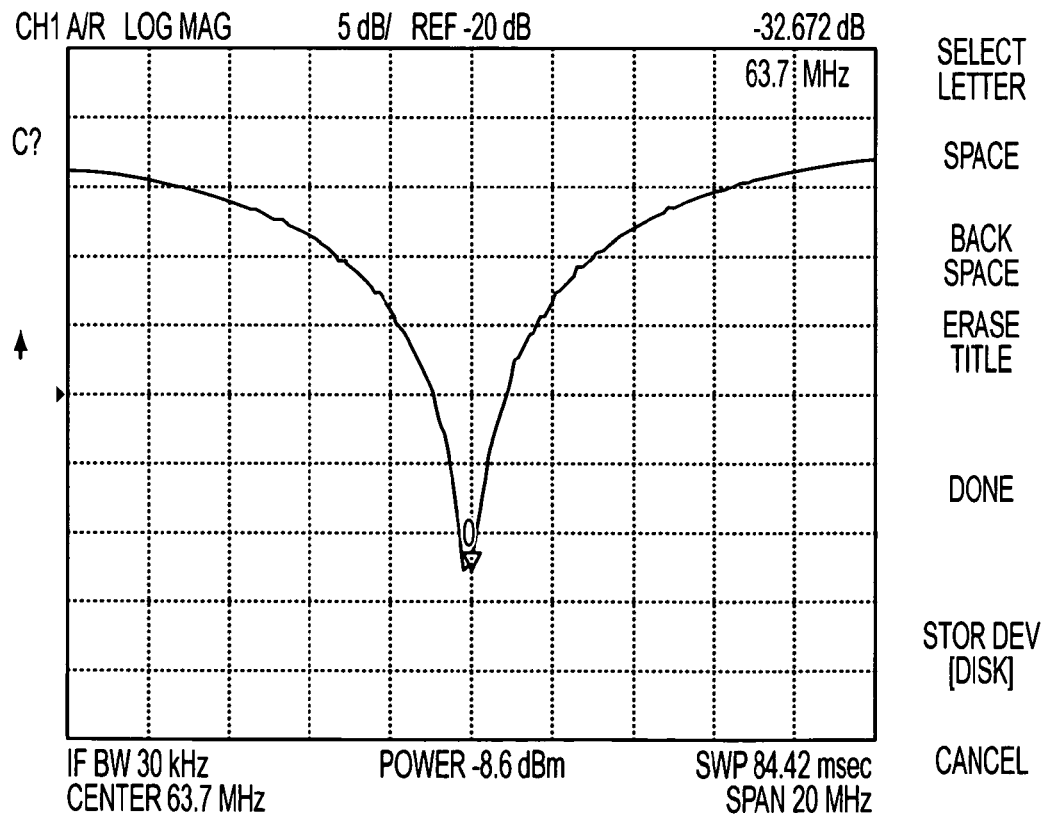
FIG. 12 is a graph that represents the reflection loss as log magnitude of a loop antenna design in which large return loss indicates a good match.

The return loss evaluates the difference between the reflected wave and the incident wave in decibels, as can be seen in FIG. 12. Return loss does not have phase information and it is primarily used in production testing where the goal is to reject assembled parts that do not meet a specified minimum limit. This limit value will be set depending on the phantom test results of the designed antenna.

The Criteria for Loop Antenna Design in an Embodiment of the Invention

When constructing MRI RF coils, the network analyzer with an S-parameter test set is an essential tool. Resonant frequency measurement, the match of the circuit to 50Ω and the Quality Factor (Q) of the circuit measurement will be used for coil performance evaluation.

Quality Factor "Q"

The Quality Factor (Q) of an MRI coil is a measure of the "quality" of the resonant circuit. The resonant circuit should respond to frequencies close to the natural frequency, in this case the Larmor frequency for the targeted MRI application, more strongly than they respond to other frequencies. The characterization of this response is called the circuit Q. Generally, the larger the Q value, the better the antenna. In other words, larger Q value also means increased SNR performance of the antenna (Hoult D I, Richards R E. The Signal-to-Noise Ratio of the Nuclear Magnetic Resonance Experiment. Journal of Magnetic Resonance 1976; 24:71-85). The Q factor can be defined in several ways mathematically. First, the Q factor can be defined as the reactance of a circuit divided by the resistance. It can also be defined as the ratio of the resonant frequency divided by the bandwidth. Using the network analyzer with an S-parameter test set, the Q of a resonant circuit can be determined using either $S_{11}$ (reflection type) and/or $S_{21}$ (forward transmission gain-type) measurement methods.

Antenna Impedance Matching

Antenna Impedance Matching is a necessary procedure to provide the maximum possible transfer of power between a source and its load. In active guidewire applications, any unnecessary loss in a circuit that is already carrying extremely small signal levels simply cannot be tolerated. Therefore, extreme care is taken during the initial design of such a front end to make sure that each device in the chain is matched to its load. In dealing with ac waveforms, the maximum transfer of power from a source to its load occurs when the load impedance ($Z_L$) is equal to the complex conjugate of the source impedance. The complex conjugate simply refers to complex impedance having the same real part with an opposite reactance. Thus, if the source impedance is $Z_s=R+jX$, then its complex conjugate would be $Z_s=R-jX$. The maximum power is transferred from a source to its load if the load resistance equals the source resistance. So, in this case maximum transfer of power does occur when the load impedance is the complex conjugate of the source. The source ($Z_s$) with a series reactive component of +jX (an inductor), is driving its complex conjugate load impedance consisting a −jX reactance (capacitor) in series with $R_L$. The +jX component of the source and −jX component of the load in series cancel each other, leaving only $R_S$ and $R_L$. Since $R_S$ and $R_L$ are equal, maximum power transfer has occurred. So in general, any source reactance is resonated with an equal and opposite load reactance; thus, leaving only equal resistor values for the source and the load terminations.

Smith Chart

Figure 13:
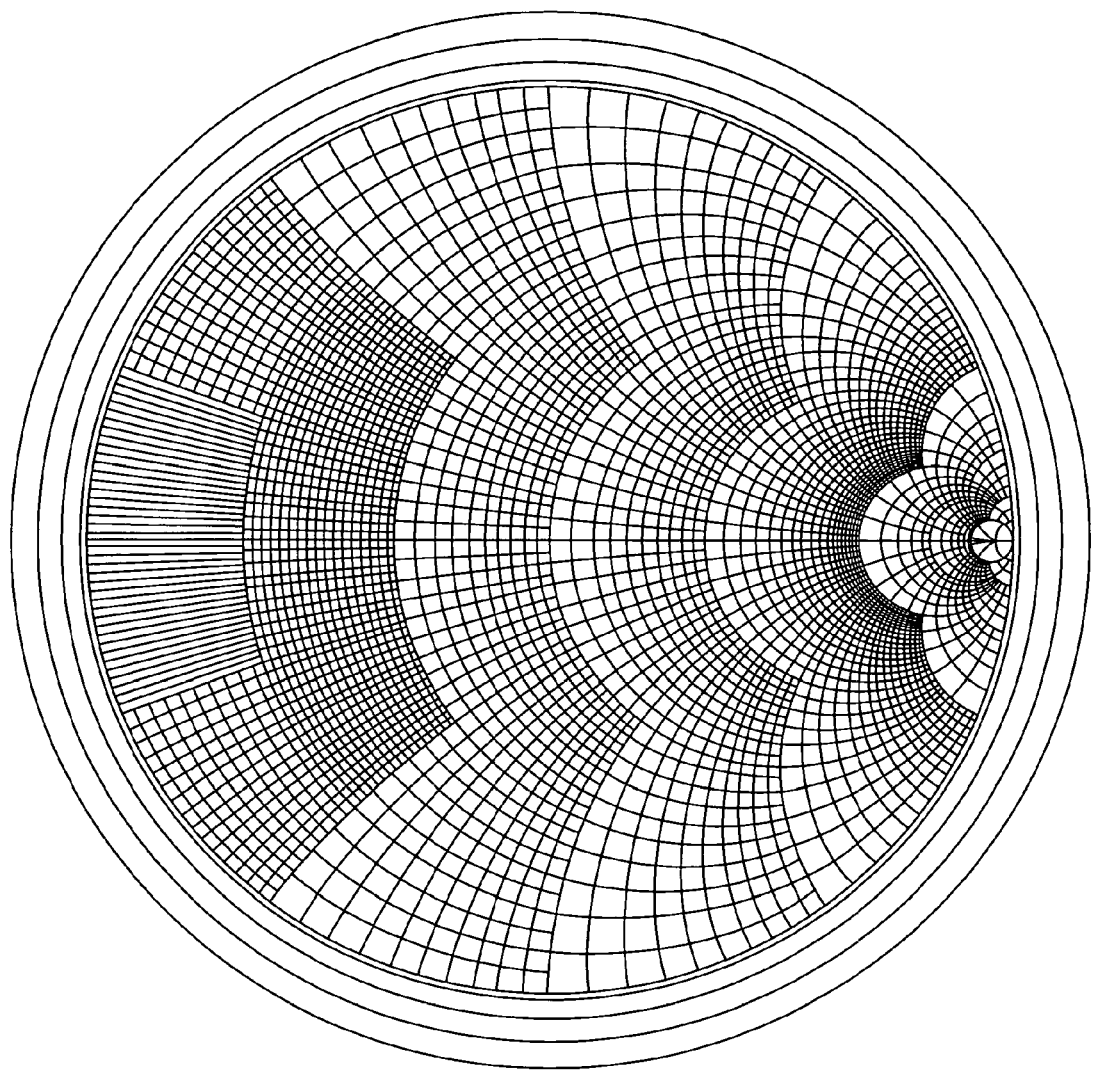
FIG. 13 is an example of a Smith Chart.

To determine the correct circuit element types and values during impedance matching, the Smith chart is a useful tool. The Smith Chart, shown in FIG. 13, has a center value of 50 ohms for the use of impedance bridges that measure directly in impedances. The Smith chart consists of a family of circles and a family of arcs which intersect each other at right angles. The circles are tangent at a common point at the right of the chart. Points along any of these circles represent the same value of resistance R. Larger circles correspond to lower values of R, down to zero for a circle equal to the chart diameter. Smaller circles represent higher values of resistance, approaching infinity as the circle becomes smaller. The family of arcs represents constant values of the reactance +jX and −jX. These arcs all pass through the point at the right of the chart, and have their radii along a vertical line passing through that point. jX equals zero at the left of the Smith chart and increases in both directions; inductive reactance +jX clockwise and capacitive reactance −jX counterclockwise. As the right of the chart is approached, both +jX and −jX increase to infinity, with the largest labeled being 2500 ohms.

There is an infinite number of possible networks which could be used to perform the impedance matching. The separate matching and detuning circuit was designed for a loop and dipole antenna.

Antenna Detuning During RF Transmission

In all MRI applications in which embedded antennas are used for signal reception, antenna detuning is necessary during RF transmission to prevent high voltages from being induced in the receiving antenna and other circuit elements. The potentially high voltages, currents, and the induced electrical fields pose a safety hazard and disrupt the desired uniform excitation field generation required for excitation. This may lead to particular localized effects in interventional MR imaging. Detuning is often achieved by applying a voltage to a special portion of the electronics of the receiver coil and causes the receiver coil's resonant frequency to change.

Matching/Detuning Design for Loop Antenna

Figure 14:
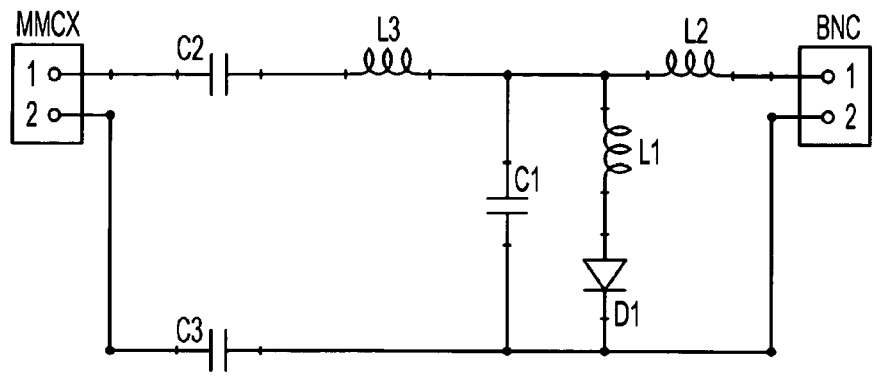
FIG. 14 is a schematic representation of a matching/detuning circuit for a loop antenna according to an embodiment of the current invention.

The below circuit in FIG. 14 shows the matching and detuning circuit designed for a loop antenna design. The loop antenna is a balanced circuit, that is, it has a return path for current if the small amount of energy radiated by the shield of the coaxial cable is ignored.

In FIG. 14, electronic components are as follows:

C2, C3: DC blocking capacitors. They are as large as 600-1000 pF. C2 is also a part of the matching network.

C1: Parallel capacitor and a part of the matching network. C1 cannot be replaced by a short circuit or an inductor.

L2, L3: Serial inductors. These inductors are part of the matching network. In case they are not needed, they should be replaced by a short circuit. L2 cannot be replaced by a capacitor, since otherwise it would block the DC voltage applied by the MR machine during transmit mode. If the value of L3 is found as capacitive rather than inductive, then C2 can be replaced by the new value of two capacitors in series and L3 with a shot circuit.

D1: Decoupling diode. It is usually a PIN diode, because the response time of the PIN diodes are very short.

L1: In parallel with C1 in transmit mode after the diode is biased and acting as short circuit for small RF voltages, forms an open circuit.

Matching/Detuning Design for Dipole Antenna

In the case of a dipole antenna, the extended inner conductor of the guidewire forms one pole. For the best radiation efficiency the whip length (extension) should be equal to λ/4. Because a loopless antenna is unbalanced, it should be connected to the balanced matching circuit via a balun. To block the unwanted generated current on the outer surface of the shield, a capacitor should be placed in parallel with the balun. The circuit designed to match and decouple the loopless antenna is shown in FIG. 15.

Figure 15:
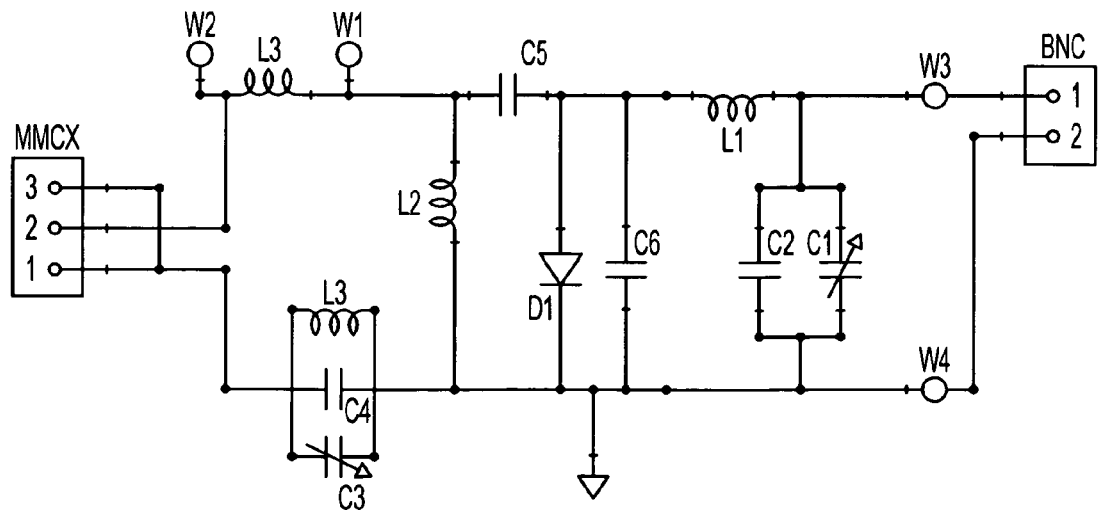
FIG. 15 is a schematic representation of a matching/detuning circuit for a dipole antenna according to an embodiment of the current invention.

In FIG. 15, electronic components are as follows:

L3: Balun constructed from a semi rigid coaxial cable. Six turns is ideal. The inner conductor experiences very little inductance.

C3, C4: To block the unwanted shield current, capacitors are placed in parallel with the balun inductor. The capacitor values are chosen such that they resonate at 63.7 MHz and behave as an open circuit.

D1: Decoupling diode. It is usually a PIN diode, because the response time of the PIN diodes are very short.

L2, C5: Decoupling network. If there is no need for L3, its place can be left free. C5 serves also for a DC block during transmission mode to prevent DC current from flowing into the antenna. Therefore, if there is no need for C5, a large capacitor (600-1000 pF) should be used.

C1, C2, L1, C6: Matching network. This network is designed to match all possible antenna impedances to 50 ohm. C6 is optional. If there is no need for C6, it can be left free. C1, being a trimmer capacitor, is required to match the impedance more precisely.

I claim:

1. A guidewire for use with interventional magnetic resonance imaging, comprising:
 a guidewire body having a distal end and a proximal end and reserving a space therein, the guidewire body having an elongated shaft between the proximal end and the distal end;
 a dipole antenna disposed in said space reserved within said guidewire body, said dipole antenna being adapted to be electrically connected to a signal processing system through a first signal channel through said proximal end of said guidewire body; and
 a loop antenna disposed in said space reserved within said guidewire body toward said distal end of said guidewire body, said loop antenna being adapted to be electrically connected to said signal processing system through a second signal channel through said proximal end of said guidewire body, the loop antenna including a micro-coil positioned adjacent the distal end of the guidewire body for providing visualization information of a tip of the guidewire;
 wherein the dipole antenna is positioned between the proximal end of the guidewire body and the micro-coil for providing visualization information of the elongated shaft;
 wherein said dipole antenna and said loop antenna are each constructed to receive magnetic resonance imaging signals independently of each other and to transmit received signals through said first and second signal channels, respectively, to be received by said signal processing system.

2. A guidewire according to claim 1, wherein said dipole antenna comprises:
 an outer hypotube disposed within said space reserved within said guidewire body;
 an inner hypotube disposed within a lumen defined by said outer hypotube; and
 an electrical insulation layer disposed between said inner hypotube and said outer hypotube,
 wherein said inner hypotube extends beyond a distal end of said outer hypotube in a direction of said distal end of said guidewire to provide a whip portion of said dipole antenna, said inner and outer hypotubes providing at least a portion of said second signal channel.

3. A guidewire according to claim 2, wherein said whip portion of said dipole antenna has a length selected to be suitable for receiving signals at a Larmour frequency during operation of a magnetic resonance imaging system.

4. A guidewire according to claim 2, wherein said inner hypotube comprises a gold surface coating thereon along the whip portion of said inner hypotube.

5. A guidewire according to claim 2, wherein said inner and outer hypotubes comprise Nitinol in a material thereof.

6. A guidewire according to claim 1, further comprising a micro-coaxial electrical cable disposed within said space reserved within said guidewire body and being electrically connected to said micro-coil, wherein said micro-coaxial electrical cable is constructed to provide at least a portion of said first signal channel.

7. A guidewire according to claim 1, further comprising a twisted pair of electrical wires disposed within said space reserved within said guidewire body and being electrically connected to said micro-coil, wherein said twisted pair of electrical wires is constructed to provide at least a portion of said first signal channel.

8. A guidewire, comprising:
 a guidewire body having an elongated shaft and a tip;
 a dipole antenna within the guidewire body, the dipole antenna electrically coupled to a dipole antenna channel; and
 a loop antenna disposed within the guidewire body, the loop antenna including a micro-coil adjacent the tip of the guidewire body and coupled to a loop antenna channel, the loop and dipole antenna channels being electrically isolated from each other so that each of the dipole antenna and the loop antenna can receive magnetic resonance imaging signals independently from each other;
 wherein the dipole antenna is positioned along the elongated shaft for providing visualization information of a majority of the elongated shaft via the dipole antenna channel and wherein the loop antenna uses the micro-coil for providing visualization information of the tip of the guidewire body via the loop antenna channel.

9. The guidewire of claim 8, wherein the dipole antenna comprises:
 an outer hypotube disposed within the guidewire body;
 an inner hypotube disposed within a lumen defined by the outer hypotube; and
 an electrical insulation layer disposed between the inner hypotube and the outer hypotube.

10. The guidewire of claim 9, wherein the inner hypotube extends beyond a distal end of the outer hypotube in a direction at an end of the guidewire body to provide a whip portion of the dipole antenna.

11. The guidewire according to claim 9, wherein the inner and outer hypotubes comprise Nitinol.

12. The guidewire according to claim 8, further comprising a micro-coaxial electrical cable disposed within the guidewire body that is electrically connected to the micro-coil.

13. The guidewire according to claim 8, further comprising a twisted pair of electrical wires within the guidewire body that are electrically connected to the micro-coil.

* * * * *